United States Patent [19]

Forsgren et al.

[11] Patent Number: 4,558,311
[45] Date of Patent: Dec. 10, 1985

[54] METHOD AND APPARATUS FOR MONITORING THE TOOL STATUS IN A TOOL MACHINE WITH CYCLIC MACHINING

[75] Inventors: Roland Forsgren, Västerås; Gunnar Garpendahl, Åkersberga; Hans Eriksson, Uppsala; Bengt Wallentin, Sollentuna, all of Sweden

[73] Assignee: KB WIBRA, Västerås, Sweden

[21] Appl. No.: 448,853

[22] PCT Filed: Apr. 13, 1982

[86] PCT No.: PCT/SE82/00120
§ 371 Date: Dec. 10, 1982
§ 102(e) Date: Dec. 10, 1982

[87] PCT Pub. No.: WO82/03589
PCT Pub. Date: Oct. 28, 1982

[30] Foreign Application Priority Data

Apr. 13, 1981 [SE] Sweden .................................. 8102372

[51] Int. Cl.⁴ ............................................. G08B 21/00
[52] U.S. Cl. ........................................ 340/680; 73/660
[58] Field of Search ............... 73/660, 659, 658, 579, 73/593; 340/680, 683

[56] References Cited

U.S. PATENT DOCUMENTS

| | | | |
|---|---|---|---|
| 2,915,897 | 12/1959 | Hoffmann | 73/659 |
| 3,277,695 | 10/1966 | Joline | 73/660 |
| 3,400,578 | 9/1968 | Frarey et al. | 73/660 |
| 4,063,450 | 12/1977 | Lyons | 73/579 |
| 4,087,801 | 5/1978 | Noh | 73/658 |
| 4,352,293 | 10/1982 | Kurihara et al. | 73/660 X |

Primary Examiner—Jerry W. Myracle
Attorney, Agent, or Firm—Witherspoon & Hargest

[57] ABSTRACT

The vibration level (a) is measured and applied to controllable filter (F). The filter (F) is a band pass filter that only passes a narrow band around a certain frequency that is determined by the frequency (1) of the machining cycle. The output signal of the filter is then compared to one or several reference levels (7) and an alarm signal is outputted in case of unacceptable deviation from the reference level.

10 Claims, 6 Drawing Figures

METHOD AND APPARATUS FOR MONITORING THE TOOL STATUS IN A TOOL MACHINE WITH CYCLIC MACHINING

The present invention relates to a method and an apparatus for monitoring the tool status in a tool machine with cyclic cutting machining, for instance a milling machine.

Within the machining industry there has been a demand for monitoring the status of the tools in continuously operating tool machines or machine tools. This monitoring shall especially include tool wear and failure. The demand for such monitoring has recently increased as the tool machines have become smaller and lighter, which has led to increased stresses on the machines. Since the power and speed also has increased the time margins for failures that previously existed have decreased. The problems are common for all cyclically operating tool machines.

The object of the present invention is to remove or reduce the problems mentioned above in connection with tool machines. Thus, the object of the invention is a method and an apparatus for monitoring the condition of the tools in cyclically operating tool machines.

Of special importance is that the method in accordance with the present invention can be applied to already installed tool machines without a radical redesign of these machines.

The objects mentioned above are arrived at with a method and an apparatus in accordance with the attached patent claims.

The invention will be described in detail under reference to the attached drawings, on which:

Figure 1:
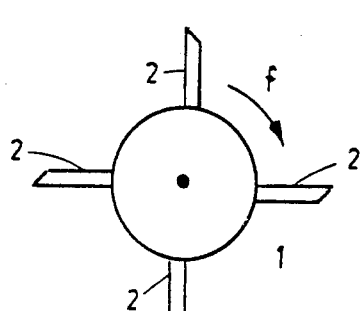
FIG. 1 is a schematic view of a work spindle of a turning machine or lathe.

FIG. 1 is a schematic view of a tool spindle 1 in for instance a milling machine (not shown). This tool spindle 1 can comprise a number of tools or cutting edges 2, in this case four cutting edges 2. It is appreciated that the number of cutting edges can vary from machine to machine and depends on work piece and process, however, for reasons of simplicity a milling machine with four cutting edges 2 will be described below. The spindle 1 rotates with speed f in the direction indicated by the arrow in FIG. 1. Thereby the cutting edges 2 will engage the work piece in succession one after the other. Thus, in this case the machining cycle comprises a one turn rotation of spindle 1. During this turn each of the four cutting edges 2 will cut the same amount of material from the work piece.

Under normal operation, that is when the cutting edges are essentially identical, properly centered and not worn out, each of the four cutting edges 2 will cut the same amount of material from the work piece. This is the ideal situation that should be aimed at. However, if one of the cutting edges 2 should be defective (worn out, tool failure) this will result in unbalance and an improper machining of the work piece. Since the defective cutting edge 2 will now cut less material than a faultless cutting edge, the following cutting edge 2 will be more heavily loaded than normal, since it now on top of its normal cutting amount also has to cut the amount of material that the defective cutting edge has left.

The above difference between normal operation and operation with defective cutting edge results in differences in vibration and impulse. These differences are, in accordance with the present invention, utilized for detecting defective cutting edges. However, a great problem has been the fact that the vibrations that result from the engagement of the tools with the work piece to a high extent disguised by other vibrations that the machine generates under normal operation and are distorted by the transmission through different machine parts between the tool or work piece and the accelerometer. Thus, the problem that is solved by the present invention is to distinguish from a vibration signal that is very noise rich and contains many signals resulting from normal operation, the essential signal component that results from the engagement of the tools with the work piece.

In accordance with the present invention some kind of sensor that converts the mechanical vibrations into electrical signals is used to measure the vibrations. Especially preferred is to use an accelerometer that easily can be placed on the frame of the machine. However, the invention is certainly not restricted to use of only this type of sensor and this location of the sensor. For instance, a position indicator or position sensor could also be utilized. Position, velocity and acceleration are different aspects of a vibration, and it is possible to convert an acceleration signal into a velocity and further into a position and vize versa. In connection with for instance a milling machine it has been found suitable to place an accelerometer (of piezo electrical type) on for instance the feed table.

Furthermore, the invention is certainly not restricted to use of only one (vibration) sensor. Thus, several (position, velocity and acceleration) sensors in different combinations can be placed on different locations on the tool machine. However, for reasons of simplicity only the use of one accelerometer arranged on the frame of the machine for the recording of a measuring signal is described below.

As was mentioned above the relevant part of the measurement will to a high extent be disguised in noise and signals resulting from normal operation. This means that the measuring signal that is produced by the sensor cannot be used directly without some form of signal processing. An idealized picture of the measuring signal is given in FIGS. 2 and 3 for normal operation and operation with defective cutting edge, respectively. The real signal will, however, contain so much noise and irrelevant signals that the peaks indicated in FIGS. 2 and 3 are difficult to recognize.

Figure 2:
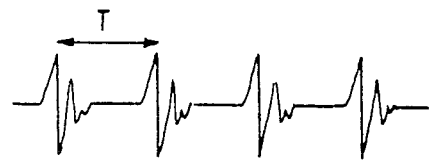
FIG. 2 is an idealized picture of the electrical measuring signal of a vibration sensor under normal operation.

Thus, FIG. 2 shows an idealized picture of the measuring signal for an operation cycle, that is for one turn of the work spindle 1. The four peaks come from the engagement of each tool with the work piece. Since FIG. 2 relates to normal operation with essentially identical tools these four peaks are essentially identical. This means that a signal with a period T is obtained, that is a signal with frequency x·f, where x is the number of fault-free cutting edges (four in this case).

Figure 3:
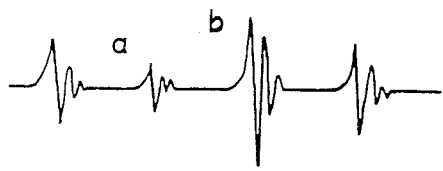
FIG. 3 is an idealized picture of the measuring signal of the vibration sensor in the case of a defective tool.

FIG. 3 shows the corresponding idealized picture of the measuring signal in case of a defective cutting edge.

The peak that corresponds to the engagement of the defective cutting edge with the work piece has been indicated by reference designation a. Since this cutting edge is defective it will not reach the work piece as it should and will therefore cut less material. The engagement is not as strong as previously, that is the amplitude becomes smaller. A consequence of this is that the following cutting edge 2 must cut more material, on the one hand the amount of material it will cut under normal operation and in addition the amount of material that the previous defective cutting edge has left. This results in a stronger engagement with the work piece, which can be seen from the higher amplitude b in FIG. 3.

A comparison between FIGS. 2 and 3 shows that the period for the signal shape of FIG. 3 is four times as long as the period T of FIG. 2. Expressed in other words, the fundamental frequency of the signal shape of FIG. 3 is f, while the fundamental frequency of the signal shape of FIG. 2 is 4f. These statements are rather idealized. In practice one will never obtain exactly identical peaks as in FIG. 2. However, during normal operation signal components with frequency 2 and 2f are weak or are not present at all, while these signal components increase in case of a defective tool. This difference is utilized in accordance with the invention to detect tool failure or a defective tool.

Figure 4:
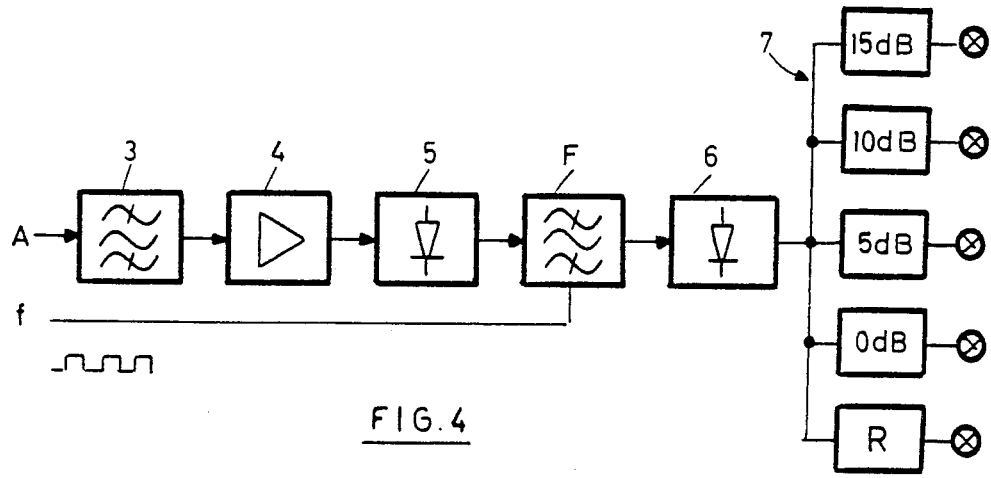
FIG. 4 is a block diagram illustrating the basic principle of the present invention.

As mentioned above, in practice one does not obtain the idealized signals according to FIGS. 2 and 3 from the sensor. Actually one obtains very noise-rich signals. These signals must be processed in some way in order to make it possible to extract the essential information of FIGS. 2 and 3. FIG. 4 shows the principles of an apparatus that does exactly this.

In order to simplify the description of FIG. 4 elements 3, 4, 5 and 6 are initially disregarded.

The signal from the sensor (accelerometer) is designated by A. The signal A is led to a band pass filter F. The band pass filter F is controllable, that is the frequency band that the filter lets through can be controlled from outside. The filter can for instance be controlled to let through a narrow frequency band around the frequency f, as is shown in FIG. 4. The signal for controlling the filter F can for instance be a square wave or a pulse train with frequency f. This signal can for instance be a speedometer signal that is obtained by an optical reader and that represents the rotational speed of the spindle. Thus, the frequency f is the repetition frequency of the machining cycle.

With the aid of the parameter f (frequency) the filter F can now be controlled to let through certain frequency bands. The fundamental frequency band around f is only one of these possible frequency bands. With the aid of the same parameter f it is actually possible to adjust the filter to let through frequency bands at frequencies 2f, 3f, etc. In other words, it is also possible to study the influence of the harmonics on the measuring signal. With the aid of the same parameter f it is also possible to adjust the filter to let through frequency bands around the subharmonics f/2, f/3, f/4, etc. Thus, with only one parameter (f) it is possible to control the filter F to let through a frequency band around a frequency that depends on the parameter f. Certainly also other frequencies than the ones mentioned above are possible, the only restriction is that they should be unambiguously dependent on the parameter f.

Since it is possible to control the filter F in the way mentioned above one can chose the frequency band that gives the most significant output signal.

In the above discussion the filter F has been a single filter that can be controlled to a certain frequency. In accordance with a further development of this idea the filter F can comprise several filter sections, so that for instance the fundamental frequency, the first overtone, the first undertone, etc. automatically can be filtered out of the input signal and then can be added again to form the output signal. Also in this case it is the parameter f that controls all of the filter sections. By measuring instead for instance the ratio between the signal f and the signal f/4 some information regarding the symmetry of the tool can be obtained.

The output signal of filter F is led to a comparator section 7, in this case comprising four comparators. The four comparators in the comparator section 7 sense the output signal of filter F and compare this signal to reference levels in each comparator at for instance 0, 5, 10 and 15 dB, respectively. If the output signal of filter F exceeds a comparator level a corresponding indication lamp connected to each comparator is turned on. By studying the "shining lamp column" it is possible to obtain an indication of the present vibration level for the machine tool. The more lamps that are turned on in this column, the higher the vibration level and the more serious is the tool failure.

If desirable the output signal from filter F can also be applied to for instances a printer for recording (block R in FIG. 4).

Tests and measurements have shown that the vibration signals in a milling machine are amplitude modulated with a signal of low frequency, which comes from the engagement of the tools with the work piece, and that this signal of low frequency is very weak. In order to obtain more reliable alarm signals the simple filtering out of the fundamental frequency described above should be supplemented by further signal processing. In the example of FIG. 4 this additional signal processing is accomplished by elements 3, 4, 5 and 6.

In order to suppress disturbing signals a pre-filtration of the output signal of the accelerometer is preferred. Below frequencies of the order of 250 Hz there are disturbing signals from for instance the power line and from the drive motor of the machine, and above frequencies of the order of 2000 Hz the natural frequency oscillations of the accelerometer start to influence the measurements. Blocking or filtering away these extreme ranges increases the signal-to-noise-ratio. For this reason a further band pass filter 3 has been connected between the accelerometer and the filter F. This band pass filter 3 filters away said extreme ranges.

Furthermore, it is preferred to have a certain degree of pre-amplification of the signal. This is done in a pre-amplifier 4 between band pass filter 3 and filter F.

Since the vibration signals are amplitude-modulated a detector, which comprises a rectifier, is interconnected between pre-amplifier 4 and filter F. Thus, the information carrying parts of the signal are obtained. The detector can be peak-value-detecting and have a rise time of approximately 1 ms and a decay time of approximately 10–50 ms.

A rectifier is preferably connected after filter F for rectifying the signal obtained from the filter.

Since filter F will give an output signal also during normal operation when the cutting edges all are intact, the comparators must be adusted in such a way that no alarm signal is obtained during normal operation. This is done by adjusting the reference level of the comparators to 0, 5, 10 and 15 dB, respectively, above the reference level of normal operation.

Figure 5:
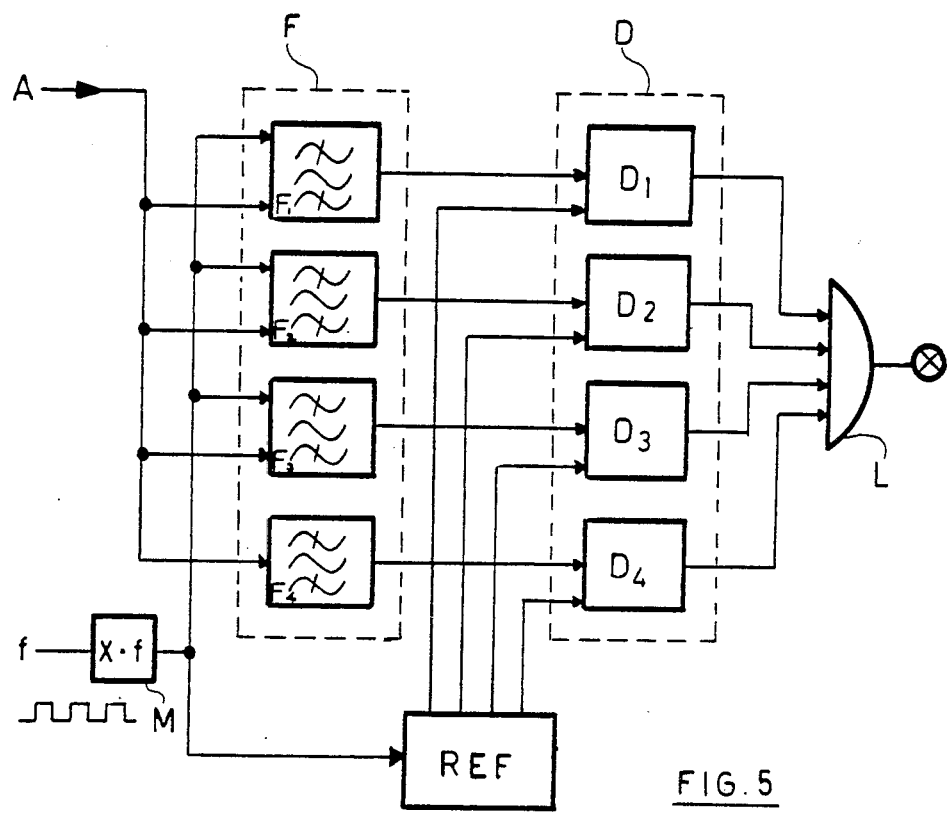
FIG. 5 is a block diagram of another embodiment of the present invention.

FIG. 5 shows an alternative embodiment of the apparatus in accordance with the present invention. For reasons of simplicity elements corresponding to elements 3, 4, 5 and 6 in FIG. 4 have been deleted in FIG. 5.

In the apparatus in accordance with FIG. 5 the accelerometer signal is applied to a filter section F, which in this case comprises four filters F1, F2, F3, F4. All of these filters are band pass filters. Filters F1, F2, F3 are controlled by the speed of the spindle over the speedometer signal f. Before this signal is applied to filter section F it is multiplied in a multiplier M by the number of cutting edges (x). The frequency obtained from the multiplier M will be called the fundamental frequency in the following description. The signal from the multiplier now controls filter F1 to pass a band at the fundamental frequency. The same signal is utilized also to control filter F2 to pass a narrow band around the first overtone (frequency $2 \cdot x \cdot f$). Furthermore, the signal is utilized to control filter F3 to pass a narrow band around the first undertone (frequency $\frac{1}{2} \cdot x \cdot f$). Finally, the filter section F comprises a filter F4, which is independent of the output signal from multiplicator M, and which only takes away the extreme frequencies, for instance the frequencies mentioned above in connection with the embodiment of FIG. 4. Thus, the last mentioned filter comprises a band pass filter with a relatively broad band as compared to filters F1, F2, F3.

The part of the apparatus in accordance with FIG. 5 that has been described until now corresponds essentially to the basic principles of the design in accordance with FIG. 4. The further development of the design in accordance with FIG. 5 comprises especially the more sophisticated reference value comparison that is performed in the design in accordance with FIG. 5. Thus, the apparatus in accordance with FIG. 5 comprises a reference value supply REF that supplies different reference values to four discriminators D1, D2, D3, D4 in a discriminator section D. These four reference values are those reference levels that would be obtained from filters F1, F2, F3, F4, respectively, during normal operation with intact tools. Thus, each discriminator D1-D4 has for instance logical 1 as output signal if the output from the corresponding filter exceeds, or alternatively with a predetermined amount exceeds, the corresponding reference value from the reference value supply REF. The four logical output signals from the discriminator section D are thereafter combined in a logical unit that can provide for instance an alarm signal to an indicator lamp if at least two of four or at least three of four discriminators have outputted alarm signals (for instance logical 1). This gives the advantage of only one lamp instead of a possibly irritating lamp column. When this single lamp shines it is clear that an alarm is really motivated.

In its simplest form the reference value supply can comprise simple potentiometers, the voltage levels of which are adjusted to the characteristics vibration levels for normal operation. In this case there is a static reference value for each test frequency.

A more sophisticated apparatus can utilize for instance a tape recorder or a computer type memory as reference value supply. In this case it is possible to give the different phases in a machining process of a work piece different reference value levels. Thus, it can be perfectly normal also with intact cutting edges that the vibration level under certain machining phases temporarily increases or decreases. In order to avoid that the apparatus under such circumstances of normal increases and decreases outputs an alarm it is preferable to apply corresponding increases and decreases in the reference value to discriminators D1, D2, D3 and D4. In this case the reference values are dynamic reference values that follow the different phases of the work process.

If the reference value supply REF is intended to provide dynamic reference values it is preferable to synchronize it with the present machining process. To obtain this function the output signal of the multiplier M can be used to control the application of the recorded reference values to the corresponding discriminator, or in connection with numerically controlled machines the control program can also control the reference value supply.

The method described above to utilize changes in characteristic frequency components for monitoring the tool status can also be expanded to contain control of the machine. Thus, the previously described alarm signals are only one example of how the information derived from the vibration signals can be used. The same information can also be used to directly control the entire process, for instance perform a tool change when a cutting edge is defect of when the cutting edges are worn out or to stop the machine on tool failure. In this case it is preferable to let for instance a microcomputer system control the entire monitoring process. A simple principle diagram for such a system is shown in FIG. 6.

Figure 6:
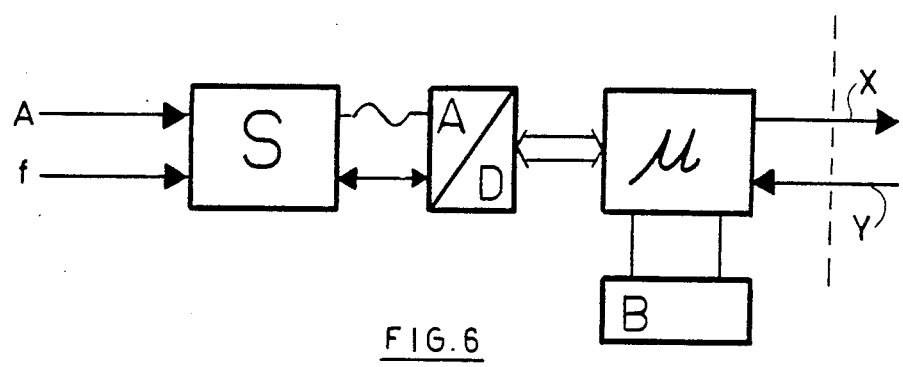
FIG. 6 shows the basic principle for a computerization of the monitoring system.

In the embodiment of FIG. 6 the signals A, f are as previously applied to the "signature analyser" S. This analyser can for instance comprise of the apparatus up to and including the band pass filter section F in FIG. 5. The analog signals from the signature analyser are applied to an A-D-converter, which forms an interphase to a computer system, for instance a microcomputer system $\mu$. The microcomputer system comprises conventional elements such as data memory, program memory, CPU+control I/O. The microcomputer system $\mu$ performs the necessary evaluation of the output signal of the signature analyser, that is the comparison with the reference levels. These can in binary form be stored directly in the data memory of the microcomputer system. In the case of dynamic reference values the data memory can for instance be divided into a sequence of data pairs, the first element in each pair referring to a predetermined discrete point of time, while the second element refers to the reference value present at said point of time for the frequency band in question. Preferably the reference values are scaled in such a way that the available quantisation levels are maximally utilized. This means that also the measuring values from the signature analyser should be scaled (damped, amplified) in a corresponding degree. The microcomputer system therefore preferably over its A-D-converter controls the amplification of the measuring signal (the double-pointed arrow between the signature analyser S and the A-D-converter).

The microcomputer system $\mu$ forms, in addition to an evaluation unit, also a control unit for the tool machine. Thus, when an alarm is released the computer system transmits a signal on line X for activation of a tool change. When the tool change has been performed the tool changing apparatus (not shown) sends a return signal (receipt) on line Y back to the computer system μ. Thereafter the machining process can continue.

The microcomputer system comprises a control unit B for external control. With this control unit the operator can order start/stop, reset the alarm and perform manual tool change. Furthermore, the operator can over the control unit program the machining process necessary for the present work piece and thereafter set the machine in monitoring mode.

The microcomputer can also be programmed to perform the entire signal analysis, that is replace all the filters, detectors and multipliers, etc. in FIGS. 4 and 5.

The present invention has been described under reference to a special tool machine, namely a milling machine. However, it is appreciated that the invention is not restricted to only milling machines but that the same principles also can be used in connection with other types of cyclically maching tool machines such as drilling machines, lathes, cutter machines or shaping machines, etc.

Furthermore, use of the spindle speed or multiples of this speed as frequency control parameters have been disclosed herein. Another equivalent parameter can be for instance motor speed (for example in connection with a drilling machine).

In certain applications it can be desirable not to release an alarm until certain secondary conditions have been fullfilled. For instance, in connection with the start of a machine it can be perfectly normal that the vibration level inertially is rather high without there being any actual fault. In these cases it is not desirable to release an alarm. As a secondary condition one can use for instance that the power or temperature of the machine must exceed a predetermined value before an alarm can be released.

In the above specification the discussion has always related to a situation in which an alarm is released when a measuring signal exceeds a reference level. In certain cases, however, it can also be useful to output an alarm when the reference level exceeds the measuring signal with a predetermined value. This can be the case for instance if the tools do not even touch the work piece. In such an embodiment an alarm should be outputted if the measuring signal differs too much from the reference signal level.

From the discussion above it is clear that the invention can be modified and varied in many ways within the basic principle. Thus, the invention is not restricted by the present specification but only by the attached patent claims.

We claim:

1. Method of monitoring the tool status in a machine tool comprising the steps of measuring the vibration level (A) of the machine tool within at least one narrow frequency band, which is controlled by the machining cycle frequency (f), and comparing the obtained vibration level to at least one corresponding reference level, an alarm signal being outputted if the detected vibration level deviates unacceptably from the reference level.

2. Apparatus for monitoring the tool status in a machine tool, comprising at least one sensor for detecting the vibrations of the machine tool, at least one band pass filter (F, F1-F3) for filtering of the signal (A) from the sensor, characterized in a frequency detector for detecting the machining cycle frequency (f) and for use in controlling the filter (F, F1-F3) in such a way that only one or several narrow frequency bands depending on said machining cycle frequency can pass through the filter, and an evaluation unit (7, D, μ) for comparing the output signals of the filter with at least one reference level and for outputting an alarm signal in case of unacceptable deviation from the reference level.

3. Apparatus in accordance with claim 2, characterized in a filter section (F) with three band pass filters (F1-F3) controlled by the machining cycle frequency.

4. Apparatus in accordance with claim 3, characterized in a storing unit (D, μ) for storing a reference level for each band pass filter (F1-F3).

5. Apparatus in accordance with claim 4, characterized in that the storing unit (D, μ) is a dynamic storing unit for storing reference levels that vary with time.

6. Apparatus in accordance with claim 5, characterized in that the sensor is an accelerometer.

7. Apparatus in accordance with claim 6, characterized in that the frequency detector is a speedometer.

8. Apparatus in accordance with claim 7, characterized in that the evaluation comprises a computer system (μ) with the aid of which measures can automatically be taken in case of unacceptable deviation from the reference level.

9. Apparatus in accordance with claim 8, characterized in that the computer is a microcomputer which provides all the controlling and signal processing means.

10. Apparatus in accordance with claim 9 for monitoring the tool status of a milling machine, characterized in that the frequency detector detects the spindle speed (f) of the milling machine.

* * * * *